United States Patent [19]
Del Corral et al.

[11] Patent Number: 5,843,865
[45] Date of Patent: Dec. 1, 1998

[54] SYNERGISTIC ANTIMICROBIAL COMPOSITIONS CONTAINING AN IONENE POLYMER AND A SALT OF DODECYLAMINE AND METHODS OF USING THE SAME

[75] Inventors: Fernando Del Corral, Memphis; Percy Jaquess, Tigrett; David Oppong, Memphis, all of Tenn.

[73] Assignee: Buckman Laboratories International, Inc., Memphis, Tenn.

[21] Appl. No.: 796,575

[22] Filed: Feb. 6, 1997

Related U.S. Application Data

[60] Provisional application No. 60/011,290 Feb. 7, 1996.

[51] Int. Cl.⁶ .......................... A01N 33/00; A01N 33/02; A01N 33/08; A61K 31/74
[52] U.S. Cl. .................. 504/160; 424/78.09; 424/78.37; 424/78.35; 504/158; 514/554; 514/556; 514/642; 514/663; 514/667
[58] Field of Search .................. 424/78.09, 78.37, 424/78.35; 514/642, 554, 556, 663, 667; 504/158, 160

[56] References Cited

U.S. PATENT DOCUMENTS

| | | | |
|---|---|---|---|
| Re. 28,808 | 5/1976 | Panzer et al. | 260/2 |
| 3,003,915 | 10/1961 | Borick et al. | 167/22 |
| 3,140,976 | 7/1964 | Berenschot et al. | 167/22 |
| 3,738,945 | 6/1973 | Panzer et al. | 260/2 |
| 3,778,476 | 12/1973 | Rembaum et al. | 260/567.6 |
| 3,874,870 | 4/1975 | Green et al. | 71/67 |
| 3,894,946 | 7/1975 | Panzer et al. | 210/54 |
| 3,894,947 | 7/1975 | Panzer et al. | 210/54 |
| 3,931,319 | 1/1976 | Green et al. | 260/567.6 P |
| 4,025,627 | 5/1977 | Green et al. | 424/248.4 |
| 4,027,020 | 5/1977 | Green et al. | 424/248.56 |
| 4,089,977 | 5/1978 | Green et al. | 424/329 |
| 4,104,161 | 8/1978 | Wein | 210/54 |
| 4,111,679 | 9/1978 | Shair et al. | 71/67 |
| 4,147,627 | 4/1979 | Goodman | 210/58 |
| 4,164,521 | 8/1979 | Goodman | 525/187 |
| 4,166,041 | 8/1979 | Goodman | 252/180 |
| 4,506,081 | 3/1985 | Fenyes et al. | 548/523 |
| 4,581,058 | 4/1986 | Fenyes et al. | 71/67 |
| 4,606,773 | 8/1986 | Novak | 106/213 |
| 4,769,155 | 9/1988 | Dwyer | 210/728 |
| 4,778,813 | 10/1988 | Fenyes et al. | 514/357 |
| 4,970,211 | 11/1990 | Fenyes et al. | 514/252 |
| 5,051,124 | 9/1991 | Pera | 71/67 |
| 5,093,073 | 3/1992 | Schenker | 376/310 |
| 5,093,078 | 3/1992 | Hollis et al. | 422/16 |
| 5,128,100 | 7/1992 | Hollis et al. | 422/14 |
| 5,142,002 | 8/1992 | Metzner | 525/540 |

FOREIGN PATENT DOCUMENTS

| | | |
|---|---|---|
| 4739337 | 10/1992 | Japan . |
| WO 95/12976 | 5/1995 | WIPO . |

*Primary Examiner*—Allen J. Robinson
*Attorney, Agent, or Firm*—Armstrong, Westerman, Hattori, McLeland & Naughton

[57] ABSTRACT

Compositions comprising an ionene polymer and a salt of dodecylamine are disclosed which are synergistically effective compared to the respective components alone in controlling the growth of microorganisms in or on a material or medium. Methods to control the growth of microorganisms with the use of the compositions of the present invention are also disclosed.

34 Claims, No Drawings

SYNERGISTIC ANTIMICROBIAL COMPOSITIONS CONTAINING AN IONENE POLYMER AND A SALT OF DODECYLAMINE AND METHODS OF USING THE SAME

CROSS-REFERENCE TO RELATED APPLICATION

This application is based on U.S. Provisional Patent Application Serial No. 60/011,290, filed Feb. 7, 1996, which is incorporated in its entirety herein by reference.

BACKGROUND OF THE INVENTION

The present invention relates to certain compositions and processes useful for controlling the growth of one or more microorganisms. The novel processes and mixtures of the present invention show unexpected synergistic activity against microorganisms, including bacteria, fungi and algae. The present invention particularly relates to the use of compositions/mixtures comprising an ionene polymer and a salt of dodecylamine.

A large number of commercial industrial and agricultural products are subject to microbiological attacks that reduce or destroy their economic value. Examples of products that may be subject to such biological fouling are coatings, wood and wood products, agricultural seed, animal hides, textiles, plastics, adhesives, pharmaceuticals, cosmetics, toiletries, lubricants, agrochemicals, petrochemicals, paints, proteinaceous materials, and the like. The storage temperature of these and other products and the products' intrinsic characteristics make them susceptible to the growth of various microorganisms. These microorganisms can be introduced during manufacturing or handling by exposure to air, tanks, pipes, equipment, humans, or any other agent or environment carrying microbiological contaminants.

Aqueous systems, such as emulsions, suspensions, or solutions containing organic materials, are also highly subject to microbiological attack. Such aqueous systems include dyes, latexes, paints, surfactants, dispersants, stabilizers, thickeners, adhesives, starches, waxes, proteins, emulsifying agents, detergents, cellulose products, resins, metalworking fluids, cooling tower fluids, paper mill liquors, tanning liquors, and recreational aqueous systems, i.e., pools, spas, etc., and the like. These systems frequently contain relatively large amounts of water, causing them to be well-suited environments for biological growth and thus attack and degradation. Microbiological fouling and degradation of aqueous systems containing organic materials manifests itself by problems such as loss of viscosity, gas formation, objectionable odors, decreased pH, emulsion breaking, color change, and gelling.

Another objectionable phenomenon occurring in aqueous industrial, commercial, or recreational systems is slime formation. Slime can reduce yields from industrial processes using aqueous systems and render recreational aqueous systems unsuitable for use. Slime consists of matted deposits of microorganisms, fibers, and debris. It may be stringy, pasty, rubbery, tapioca-like, or hard, and may have a characteristic undesirable odor that is different from that of the aqueous liquid system in which it is formed. The microbiological contaminants involved in slime formation are primarily different species of spore-forming and nonspore-forming bacteria, particularly capsulated forms of bacteria that secrete gelatinous substances that envelop or encase the cells. Slime microorganisms also include filamentous bacteria, filamentous fungi of the mold type, yeasts, and yeast-like organisms.

The microbiological organisms responsible for biological fouling of various aqueous systems include various bacteria, fungi, mildews, algaes, and the like. To control deterioration or degradation caused by microorganisms, various industrial microbicides are used. Workers in the trade have continued to seek improved biocides that have low toxicity and are capable of exhibiting a prolonged biocidal effect against a wide variety of microorganisms at normal use. Increasingly stringent environmental and safety regulations as well as escalating development costs have created the need for new microbicidal agents selected from known safe and economical materials.

Primary alkyl carboxylic acid salts are known to have surfactant properties arising from the hydrophobic apolar hydrocarbon chain and the hydrophilic polar amine acid group; however, the utility and effectiveness of these compounds as microbicides and herbicides has not been known or appreciated in the prior art.

Ionene polymers, i.e., cationic polymers containing quaternary nitrogens in the polymer backbone, is one group of biocides used in controlling bacteria and algae in various aqueous systems. See, e.g., A. Rembaum, "Biological Activity of Ionene Polymers," Applied Polymer Symposium No. 22, 299–317 (1973) and 0. May, Polymeric Antimicrobial Agents" in Disinfection, Sterilization, and Preservation, S. Block, ed., 322–333 (Lea & Febiger, Philadelphia, 1991). Ionene polymers have a variety of uses, in aqueous solutions such as microbicides, bactericides, and algicides as well as controlling, even preventing, biofilm and slime formation. U.S. Pat. Nos. 3,874,870; 3,931,319; 4,027,020; 4,089,977; 4,111,679; 4,506,081; 4,581,058; 4,778,813; 4,970,211; 5,051,124; 5,093,078; 5,142,002; and 5,128,100, the disclosure of each of which is incorporated here by reference, give various examples of these polymers, their preparation, and their uses. While generally effective as algicides and bactericides, most ionene polymers are less effective against many groups of fungi.

Accordingly, there is a need in the art for a microbicidal composition that overcomes these and other problems.

SUMMARY OF THE INVENTION

It is therefore an object of this invention to provide a microbicidal composition capable of controlling the growth of at least one microorganism, particularly fungi, bacteria and algae over prolonged periods of time. It is an additional object to provide such compositions which are economical to use. Methods of controlling the growth of at least one microorganism are also objects of this invention.

According to the present invention, controlling the growth of at least one microorganism includes both the reduction and/or prevention of such growth. It is to be further understood that by "controlling" the growth of at least one microorganism, the growth of at least one microorganism is inhibited. In other words, there is no growth or substantially no growth of at least one microorganism. "Controlling" the growth of at least one microorganism includes maintaining a microorganism population at a desired level (including undetectable levels such as zero population), reducing a microorganism population to a desired level and/or inhibiting or slowing the growth of at least one microorganism. Thus, materials and media susceptible to attack by at least one microorganism are preserved and/or protected from this attack and the resultant deleterious effects.

In accordance with these and other objects, the present invention provides a composition comprising an ionene polymer and a salt of dodecylamine where the components are present in a combined amount synergistically effective to control the growth of at least one microorganism.

The present invention also provides a method for controlling the growth of at least one microorganism in or on a material or medium susceptible to attack by the microorganism which comprises the step of adding to the material or medium a composition of the present invention in an amount synergistically effective to control the growth of the microorganism. The synergistically effective amount varies in accordance with the material or medium to be treated and can, for a particular application, be routinely determined by one skilled in the art.

The present invention also embodies the separate addition of an ionene polymer and a salt of dodecylamine to the products, materials or media described above. According to this embodiment, the components are individually added to the system so that the final amount present at the time of use is that amount synergistically effective to control the growth of at least one microorganism.

The compositions of the present invention are also useful in preserving or controlling the growth of microorganisms in various types of industrial media or materials susceptible to attack by microorganisms. Such media or materials include, but are not limited to, dyes, pastes, lumber, leather, textiles, pulp, wood chips, tanning liquor, a paper mill liquor, a polymer emulsion, a paint, paper and other coating and sizing agents, a metalworking fluid, a geological drilling lubricant, petrochemicals, a cooling water system, recreational water, influent plant water, waste water, pasteurizers, retort cookers, a pharmaceutical formulation, and cosmetic and toiletry formulations.

The composition can also be useful in agrochemical formulations for the purpose of protecting seeds or crops against microbial spoilage.

Additional objects and advantages of the invention will be set forth in part in the description which follows, and in part will be apparent from the description, or may be learned by the practice of the invention. The objects and advantages of the invention may be realized and obtained by means of the elements and combinations particularly pointed out in the claims.

It is to be understood that both the foregoing general description and the following general description are exemplary and explanatory only and are not restrictive of the present invention as claimed.

DETAILED DESCRIPTION OF PREFERRED EMBODIMENTS

When two chemical microbicides are combined into one product or added separately three results are possible:

1) The resulting product would produce an additive (neutral) effect.
2) The products in the product would produce an antagonistic effect, or
3) The chemicals in the product would produce a synergistic effect.

An additive effect has no economic advantage over the individual components. The antagonistic effect would produce a negative impact. Only synergistic effect, which is less likely than either an additive or antagonistic effect, would produce a positive effect and therefore possess economic advantages.

It is known in the microbicidal literature that there is no theoretical method to anticipate additive, antagonistic or synergistic effects when two biocides are mixed to yield a new formulation. Nor is there a method to predict the relative proportions of the different biocides required to produce one of the three effects described above.

The inventive microbicidal compositions combining an ionene polymer and a salt of dodecylamine demonstrate an unexpected synergistic effect compared to the respective components alone. Thus, these compositions achieve superior, i.e. greater than additive, microbicidal activity, even at low concentrations, against a wide variety of microorganisms. Examples of these microorganisms include fungi, bacteria and algae such as *Trichoderma harzianun, Pseudomonas aeruginosa* and *Chlorella pyrenoidosa*. Preferably, the compositions of the present invention have a low toxicity.

Any ionene polymer or mixture of ionene polymers may be used to practice this invention. Ionene polymers may be classified according to the repeating unit found in the polymer. The repeating unit results from the reactants used to make the ionene polymer.

A first preferred type of ionene polymer comprises the repeating unit of formula I:

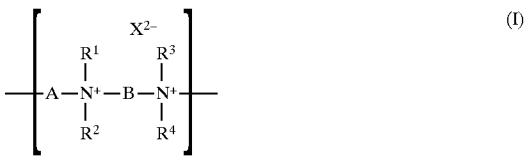

In this formula, $R^1$, $R^2$, $R^3$, and $R^4$ can be identical or different, and are selected from H, $C_1$–$C_{20}$ alkyl optionally substituted with at least one hydroxyl group, and benzyl optionally substituted on the benzene moiety with at least one $C_1$–$C_{20}$ alkyl group. Preferably, $R^1$, $R^2$, $R^3$ and $R^4$ are all methyl or ethyl.

The group "A" is a divalent radical selected from $C_1$–$C_{10}$ alkylene, $C_2$–$C_{10}$ alkenylene, $C_1$–$C_{10}$ alkynylene, $C_1$–$C_{10}$ hydroxyalkylene, symmetric or asymmetric di-$C_1$–$C_{10}$-alkylenether, arylene, arylene-$C_1$–$C_{10}$-alkylene, or $C_1$–$C_{10}$-alkylenearyl-$C_1$–$C_{10}$ alkylene. Preferably, "A" is a divalent $C_1$–$C_5$ alkylene, $C_2$–$C_5$ alkenylene, $C_2$–$C_5$ hydroxyalkylene, or symmetric di-$C_2$–$C_5$-alkylenether, and most preferably "A" is —$CH_2CH_2CH_2$—, —$CH_2CH(OH)CH_2$— or —$CH_2CH_2OCH_2CH_2$—.

The group "B" is a divalent radical selected from $C_1$–$C_{10}$ alkylene, $C_2$–$C_{10}$ alkenylene, $C_2$–$C_{10}$ alkynylene, $C_1$–$C_{10}$ hydroxyalkylene, arylene, arylene-$C_1$–$C_{10}$-alkylene, or $C_1$–$C_{10}$-alkylenearyl-$C_1$–$C_{10}$-alkylene. Preferably, "B" is $C_1$–$C_5$; alkylene, $C_2$–$C_5$ alkenylene, $C_2$–$C_5$ hydroxyalkylene, arylene, arylene-$C_1$–$C_5$-alkylene, or $C_1$–$C_5$-alkylenearyl-$C_1$–$C_5$-alkylene. Most preferably "B" is —$CH_2CH_2$—, —$CH_2CH_2CH_2$—, —$CH_2CH_2CH_2CH_2$—, or —$CH_2(CH_2)_4CH_2$—.

The counter ion, $X^{2-}$, is a divalent counter ion, two monovalent counter ions, or a fraction of a polyvalent counter ion sufficient to balance the cationic charge in the repeating unit which forms the ionene polymer backbone. Preferably, $X^{2-}$ is two monovalent anions selected from a halide anion and a trihalide anion and more preferably, chloride or bromide. Ionene polymers having trihalide counter ions are described in U.S. Pat. No. 3,778,476, the disclosure of which is incorporated here by reference.

The ionene polymers having the repeating unit of formula I may be prepared by a number of known methods. One method is to react a diamine of the formula $R^1R^2N$—B—$NR^1R^2$ with a dihalide of the formula X—A—X. Ionene polymers having this repeating unit and methods for their preparation are described, for example, in U.S. Pat. Nos. 3,874,870; 3,931,319; 4,025,627; 4,027,020; 4,506,081; and 5,093,078, the disclosure of each of which is incorporated here by reference. The biological activity of ionene polymers having the repeating unit of formula I is also described in these patents.

Among the ionene polymers with a repeating unit of formula I, a particularly preferred ionene polymer is poly [oxyethylene-(dimethyliminio)ethylene(dimethyliminio) ethylene] dichloride. In this ionene polymer of formula I, $R^1$, $R^2$, $R^3$ and $R^4$ are each methyl, A is —$CH_2CH_2OCH_2CH_2$—, B is —$CH_2CH_2$— and $X^{2-}$ is 2 Cl⁻, and the average molecular weight is 1,000–5,000. This ionene polymer is available from Buckman laboratories, Inc. of Memphis, Tenn. as BUSAN® 77 product or WSCP® product, which are each 60% aqueous dispersions of the polymer. BUSAN® 77 and WSCP® are biocides used primarily in aqueous systems, including metalworking fluids, for tnicroorganism control.

Another particularly preferred ionene polymer having a repeating unit of formula I is the ionene polymer where $R^1$, $R^2$, $R^3$ and $R^4$ are each methyl, A is —$CH_2CH(OH)CH_2$—, B is —$CH_2CH_2$— and $X^{2-}$ is 2 Cl⁻. This ionene polymer is a reaction product of N,N,N',N'-tetramethyl-1,2-ethanediamine with (chloromethyl)oxirane, and has an average molecular weight of 1,000–5,000. The polymer is available from Buckman Laboratories, Inc. as BUSAN® 79 product and WSCP® II product, which are each 60% aqueous solutions of the polymer.

A second type of ionene polymer comprises the repeating unit of formula II:

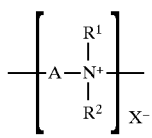

In formula II, the definitions of $R^1$, $R^2$, and A are the same as those defined above for formula I. $X^-$ is a monovalent counter ion, one half of a divalent counter ion, or a fraction of a polyvalent counter ion sufficient to balance the cationic charge of the repeating unit which forms the ionene polymer. $X^-$ may be, for example, a halide or trihalide anion, and $X^-$ is preferably chloride or bromide.

The ionene polymers having the repeating unit of formula II may be prepared by known methods. One method is to react an amine of the formula $R^1R^2NH$ with a haloepoxide such as epichlorohydrin. Ionene polymers having the repeating unit of formula II are described, for example, in U.S. Pat. Nos. 4,111,679 and 5,051,124, the disclosure of each of which is incorporated here by reference. The biological activity of ionene polymers having the repeating unit of formula II is also described in these patents.

Preferred ionene polymers having the repeating unit of formula II are those where $R^1$ and $R^2$ are each methyl, A is —$CH_2CH(OH)CH_2$—, and $X^-$ is Cl⁻. This polymer is obtained as a reaction product of N-dimethylamine with (chloromethyl)oxirane, and has an average molecular weight of 2,000–10,000. The polymer is available from Buckman Laboratories, Inc. as the BUSAN® 1055 product, a 50% aqueous dispersion of the polymer.

Another preferred ionene polymer having the repeating unit of formula II is obtained as a reaction product of dimethylamine with eichlorohydrin, where $R^1$ and $R^2$ are each methyl, A is and —$CH_2CH(OH)CH_2$— and $X^-$ is Cl⁻. This ionene polymer has a 5,000–10,000 average molecular weight, and is available from Buckman Laboratories, Inc. in a 50% aqueous solution as the BUSAN® 1055 product.

A third type of ionene polymer comprises a repeating unit of formula III:

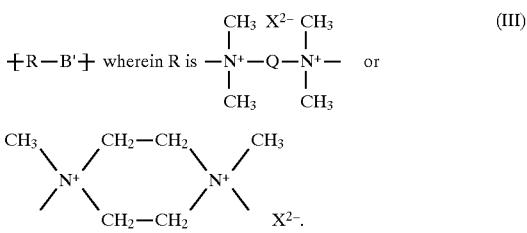

The group Q is —$(CHR')_p$—, —$CH_2$—CH=CH—$CH_2$—, —$CH_2$—$CH_2$—O—$CH_2$—$CH_2$—, —$CH_2$—CH(OH)—$CH_2$, or —$(CHR')_n$—NH—C(O)—NH$(CHR')_n$—. The group B' is $\{$—$[CH_2$—CH(OH)—$CH_2$—$N^+R'_2$—$(CHR')_n$—NH—C(O)—NH$]$—, $X^-\}$ or $\{$—$[(CHR')_n$—$N^+R_2$—$CH_2$—CH(OH)—$CH_2]$—, $X^-\}$. The variables n and p independently vary from 2 to 12. Each R' is independently hydrogen or a lower alkyl group. $X^{2-}$ is a divalent counter ion, two monovalent counter ions, or a fraction of a polyvalent counter Ion sufficient to balance the cationic charge in the group R. X is a monovalent counter ion, one half of a divalent counter ion or a fraction of a polyvalent counter ion sufficient to balance the cationic charge in the group B'.

Preferably, R' is hydrogen or $C_1$–$C_4$ alkyl, n is 2–6, and p is 2–6. Most preferably, R' is hydrogen or methyl, n is 3 and p is 2. Preferred counter ions for $X^{2-}$ and X are the same as those discussed above for formulae I and II.

The polymers of formula III are derived by known methods from bis-(dialkylaminoalkyl) ureas, which are also known as urea diamines. Ionene polymers of the formula III, methods of their preparation, and their biological activities are described in U.S. Pat. No. 4,506,081, the disclosure of which is incorporated here by reference.

Preferred ionene polymers having the repeating unit of formula III are those where R is urea diamine and B' is $CH_2CH(OH)CH_2$, and $X^-$ is Cl⁻. Available from Buckman Laboratories, Inc., ASTAT product and BL® 1090 product are 50% aqueous dispersions of this ionene polymer. The ionene polymer is obtained as a reaction product of N,N'-bis-[1-(3-(dimethylamino)-propyl)] urea and epichlorohydrin, such ionene polymer having an average molecular weight of 2,000–15,000, preferably 3,000–7,000.

Ionene polymers comprising the repeating units of formulae I, II, and III may also be cross-linked with primary, secondary or other polyfunctional amines using means known in the art. Ionene polymers can be cross-linked either through the quaternary nitrogen atom or through another functional group attached to the polymer backbone or to a side chain.

Cross-linked ionene polymers, prepared using cross-linking co-reactants, are disclosed in U.S. Pat. No. 3,738,945 and Reissue U.S. Pat. No. 28,808, the disclosure of each which is incorporated here by reference. The Reissue Patent describes the cross-linking of ionene polymers prepared by the reaction of dimethylamine and epichlorohydrin. The cross-linking co- reactants listed are ammonia, primary amines, alkylenediamines, polyglycolamines, piperazines, heteroaromatic diamines and aromatic diamines.

U.S. Pat. No. 5,051,124, the disclosure of which is incorporated here by reference, describes cross-linked ionene polymers resulting from the reaction of dimethylamine, a polyfunctional amine, and epichlorohydrin. U.S. Pat. No. 5,051,124 also describes methods of inhibiting the growth of microorganisms using such cross-linked ionene polymers. Other examples of various cross-linked ionene polymers and their properties are provided in U.S. Pat. Nos. 3,894,946; 3,894,947; 3,930,977; 4,104,161; 4,164,521; 4,147,627;

4,166,041; 4,606,773; and 4,769,155, the disclosures of each of which is incorporated here by reference.

A preferred cross-linked ionene polymer has a repeating unit of formula II. This ionene polymer is obtained as a reaction product of dimethylamine with epichlorohydrin, cross-linked with ethylenediamine, where $R^1$ and $R^2$ are each methyl, A is —$CH_2CH(OH)CH_2$— and $X^-$ is $Cl^-$. The ionene polymer has a 100,000–500,000 average molecular weight, and is available from Buckman Laboratories, Inc. in a 50% aqueous dispersion as BUSAN® 1157 product.

Another preferred cross-linked ionene polymer has a repeating unit of formula II, where $R^1$ and $R^2$ are each methyl, A is —$CH_2CH(OH)CH_2$—, and $X^-$ is $Cl^-$. The ionene polymer is cross-linked with ammonia. This ionene polymer has a molecular weight of approximately 100,000–500,000, and is available from Buckman Laboratories, Inc. in a 50% aqueous dispersion sold as the BL® 1155 product.

Buckman Laboratories, Inc. products BUSAN® 1099 or BUBOND® 65 are 25% aqueous dispersions of a cross-linked ionene polymer having repeating units of formula II, where $R^1$ and $R^2$ are each methyl, A is —$CH_2CH(OH)CH_2$—, $X^-$ is $Cl^-$, and the cross-linking agent is monomethylamine. This preferred ionene polymer has a molecular weight of approximately 10,000–100,000.

The ionene polymers comprising the repeating units of formulae I, II, or III may also be capped, i.e., have a specific end group. Capping may be achieved by means known in the art. For example, an excess of either reactant used to make the ionene polymer can be employed to provide a capping group. Alternatively, a calculated quantity of a monofunctional tertiary amine or monofunctional substituted or unsubstituted alkyl halide can be reacted with an ionene polymer to obtain a capped ionene polymer. Ionene polymers can be capped at one or both ends. Capped ionene polymers and their microbicidal properties are described in U.S. Pat. Nos. 3,931,319 and 5,093,073, the disclosure of each of which is incorporated here by reference.

Each of the above ionene polymers and products identified by trade name is available from Buckman Laboratories International, Inc. of Memphis Tenn.

The salts of dodecylamine employed in the present invention preferably have the following general formula:

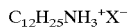

$$C_{12}H_{25}NH_3^+X^-$$

in which X is an anion or a fraction of a polyvalent counter ion sufficient to balance the cationic charge in the dodecylamine. X is preferably the conjugate base of an organic or inorganic acid, i.e., X is derived from an organic or inorganic acid by loss of an ionizable proton. Illustrative examples of suitable organic acids are the mono- and di-carboxylic acids; suitable inorganic acids include the hydrohalide acids, such as hydrochloric acid.

Preferably, X is derived from an acyclic, cyclic, or aromatic mono- or dicarboxylic acid. The carboxylic acid preferably has up to ten carbon atoms. If cyclic or aromatic, the ring may contain one or more heteroatoms, such as N, O, or S.

The carboxylic acid may also be substituted by any suitable substituent that does not adversely effect the activity of the inventive compositions. Illustrative examples of suitable substituents include alkyl groups, substituted alkyl groups, alkenyl groups, substituted alkenyl groups, amino groups, oxo groups, halogen atoms, etc.

Illustrative examples of useful carboxylic acid groups include: acetyl, propionyl, butyryl, citral, lactyl, valeryl, phthalyl, succinyl, octanoyl, nonanoyl, formyl, sorbyl, oxalyl, lauryl, and benzoyl. One of ordinary skill will recognize that other organic acid groups may also be used in the present invention.

The dodecyl group of the dodecylamine may be branched or unbranched, i.e., straight chain. Preferably, the dodecyl group is unbranched.

The dodecyl group may be unsubstituted or substituted by one or more substituents that do not adversely effect the activity of the inventive salts. Illustrative examples of suitable substituents include alkyl groups, alkenyl groups, alkoxy groups, aryl groups, aralkyl groups, hydroxy groups, oxo groups (to form a ketone), acid groups and derivatives thereof, such as esters and amides, and halogen atoms. Preferably, the dodecyl group is unsubstituted.

One or more of the hydrogen atoms bound to the nitrogen atom may be replaced by a suitable substituent to give a secondary, tertiary, or quaternary amine salt of dodecylamine. Preferably, a primary amine salt of dodecylamine is employed in the inventive compositions.

The following carboxylic acid salts of dodecylamine are particularly preferred in the practice of the present invention: dodecylamine acetate, dodecylamine propionate, dodecylamine butyrate, dodecylamine citrate, dodecylamine lactate, dodecylamine valerate, dodecylamine phthalate, dodecylamine succinate, dodecylamine octanoate, dodecylamine nonanate, dodecylamine formate, dodecylamine sorbate, dodecylamine oxalate, dodecylamine laurate, dodecylamine benzoate, dodecylamine 2-hydroxybenzoate, dodecylamine 3-hydroxybenzoate, or dodecylamine 4-hydroxybenzoate. More particularly preferred of these compounds are dodecylamine acetate, dodecylamine propionate, dodecylamine butyrate, dodecylamine valerate, dodecylamine phthalate, dodecylamine succinate, dodecylamine citrate, and dodecylamine lactate. Most particularly preferred is dodecylamine acetate.

The salts of dodecylamine are preferably prepared by reacting dodecylamine with the desired acid in the presence of a suitable solvent. Suitable acids groups are available in their acid or salt form either commercially from laboratory supply houses or can be prepared from readily available starting materials using well-known literature methods.

The synthesis of the amine salts generally can be carried out in a solvent which may be a solvent for at least one of the reactants but which is generally a solvent for the desired product. Preferred solvent systems include inorganic acids and organic acids or alcohols. Most preferred is acetic acid.

The temperature of reaction may be readily determined by one skilled in the art depending on the particular reactants employed. Preferably the temperature of reaction varies from 40° C. to 110° C. or more, more preferably the temperature of the reaction is between 70° C. and 100° C. The reaction is allowed to proceed until complete, as shown, for example, by a pH meter (the reaction is complete when the pH meter indicates that the limiting reactant has been neutralized). Generally, the reaction is stirred for 30 min to 2 hours, preferably for about 1 to 2 hours.

After the reaction is complete, the reaction product can be worked up using well-known techniques to isolate and purify the desired salt of dodecylamine. Excess reactants and any solids formed during the reaction can be filtered off, and the filtrate evaporated to yield the crude product. In cases where the desired salt compound is a solid, the product of the reaction can be recrystallized from an appropriate solvent to yield a more pure compound. It should be noted, however, that both pure and crude salts of dodecylamine can be used for in the compositions and methods of this invention. The preparation of the salts is not limited to the exact process or steps described above. Any of procedures known to the art which yield the desired end product may be used.

The particular salt of dodecylamine employed may be selected based on the compatibility of these compounds with the materials or media. Compatibility is determined by criteria such as solubility in the fluid system and lack of reactivity with the fluid or material or media in question. The compatibility is readily determined by one ordinary skill by adding the salt of dodecylamine to the material or media to be used. When used in a fluid system it is preferable that the salt of dodecylamine be freely soluble in the particular fluid resulting in a uniform solution or dispersion.

As described above, components (a) and (b) are used in synergistically effective amounts. The weight ratios of (a) to (b) vary depending on the type of microorganisms and material or media to which the composition is applied. One skilled in the art can readily determine without undue experimentation, the appropriate weight ratios for a specific application. The ratio of component (a) to component (b) preferably ranges from 1:99 to 99:1, more preferably from 1:30 to 30:1, and most preferably 1:2 to 2:1.

Depending upon the specific application, the composition may be prepared in liquid form by dissolving the composition in water or in an organic solvent, or in dry form by adsorbing onto a suitable vehicle or it can be compounded into a tablet form. The preservative may be prepared in an emulsion form by emulsifying it in water, or if necessary, by adding a surfactant. Additional chemicals, such as insecticides, may be added to the foregoing preparations depending upon the intended use of the preparation.

The mode as well as the rates of application of the composition of this invention could vary depending upon the intended use. The composition could be applied by spraying or brushing onto the material or product. The material or product in question could also be treated by dipping in a suitable formulation of the composition. In a liquid or liquid-like medium, the composition could be added into the medium by pouring, or by metering with a suitable device so that a solution or a dispersion of the composition could be produced.

The synergistic activity of the combinations described above has been confirmed using standard laboratory techniques as illustrated below. Synergism was demonstrated by the method described by Kull, E. C., Eisman, P. C., Sylwestrwicz, H. D., and Mayer, R. L., *Applied Microbiology* 9: 538–541 (1961):

$$QA/Qa + QB/Qb$$

wherein

Qa=Concentration of compound A in parts per million, acting alone, which produced an end point.

Qb=Concentration of compound B in parts per million, acting alone, which produced an end point.

QA=Concentration of compound A in parts per million, in the mixture, which produced an end point.

QB=Concentration of compound B in parts per million, in the mixture, which produced an end point.

When the sum of QA/Qa and QB/Qb is greater than one, antagonism is indicated and when the sum is equal to one, additivity is indicated. When the sum of this value is less than one, synergism exists.

This procedure for demonstrating synergism of the compositions of this invention is a widely used and acceptable procedure. More detailed information is provided in the article by Kull et al. Further information concerning this procedure is contained in U.S. Pat. No. 3,231,509, the disclosure of which is herein incorporated by reference.

Based on the above criteria, a synergistic activity against bacteria, fungi and algae is observed when an ionene polymer is combined with a salt of dodecylamine. Examples showing synergistic results can be found in the following Tables.

TABLE 1

Synergistic and additive effect of polyquat combinations with dodeclyamine acetate versus selected algae species.

| Test Organism | Quantities Producing End Points (ppm) | | | | | | |
|---|---|---|---|---|---|---|---|
| | Qa | QA | Qb | QB | QA/Qa | QB/Qb | (QA/Qa) + (QB/Qb) |
| Chlorella pyrenoidosa | 2.5 | 1.25 | 5 | 2.5 | 0.5 | 0.5 | 1.0 |
| Ulothrix gigas | 5 | 2.5 | 5 | 2.5 | 0.5 | 0.5 | 1.0 |
| | 5 | 1.25 | 5 | 2.5 | 0.25 | 0.5 | 0.75 |
| | 5 | 2.5 | 5 | 1.25 | 0.5 | 0.25 | 0.75 |
| | 5 | 2.5 | 5 | 0.6 | 0.5 | 0.125 | 0.6 |
| Chlorococcum inumdatum | 1.2 | 0.6 | 5 | 2.5 | 0.5 | 0.5 | 1.0 |
| Unknown Mixed Cooling Tower Algae | 10 | 5.0 | 2.5 | 1.25 | 0.5 | 0.5 | 1.0 |
| | 10 | 2.5 | 2.5 | 1.25 | 0.25 | 0.5 | 0.75 |

Qa = DDA alone
QA = DDA in combination
Qb = WSCP alone
QB = WSCP in combination

TABLE 2

Synergistic and additive effect of BUSAN 1055 with dodecylamine propionate versus selected algae species

| Test Organism | Quantities Producing End Points (ppm) | | | | | | |
|---|---|---|---|---|---|---|---|
| | Qa | QA | Qb | QB | QA/Qa | QB/Qb | (QA/Qa) + (QB/Qb) |
| Chlorella pyrenodiosa | 10 | 2.5 | 5 | 2.5 | 0.25 | 0.5 | 0.75 |
| | 10 | 5 | 5 | 1.25 | 0.5 | 0.25 | 0.75 |
| | 10 | 5 | 5 | 0.6 | 0.5 | 0.12 | 0.62 |
| | 10 | 5 | 5 | 0.3 | 0.5 | 0.06 | 0.44 |
| | 10 | 5 | 5 | 0.15 | 0.5 | 0.03 | 0.53 |
| Scenesdesmus obliquos | 5 | 2.5 | 5 | 2.5 | 0.5 | 0.5 | 1.0 |
| Coccomyxa simplex | 10 | 5 | 2.5 | 1.25 | 0.5 | 0.5 | 1.0 |

Qa = Dodecylamine propionate alone
QA = Dodeclyamine propionate in combination
Qb = BUSAN 1055 alone
QB = BUSAN 1055 in combination In general, however, an effective fungicidal, bactericidal or algicidal response can be obtained when the synergistic combination is employed in concentrations ranging preferably from about 0.01 ppm to about 1% (i.e., about 10,000 ppm) of the ionene polymer, more preferably about 0.1 to about 5000 ppm, and most preferably about 0.1 ppm to about 1000 ppm, and preferably from about 0.01 to about 5000 p pm of the salt of dodecylamine, more preferably about 0.1 to about 2000 ppm, and most preferably about 0.1 to about 1000 ppm.

What is claimed is:

1. A composition comprising (a) an ionene polymer and (b) a salt of dodecylamine, wherein components (a) and (b) are present in a synergistically microbicidally effective combined amount to control the growth of at least one microorganism, wherein the ionene polymer comprises the repeating unit of formula I:

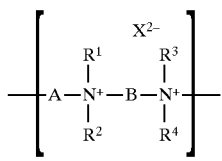

wherein

R$^1$, R$^2$, R$^3$, and R$^4$ are identical or different, and are selected from hydrogen, C$_1$–C$_{20}$ alkyl optionally substituted with at least one hydroxyl group, or benzyl optionally substituted on the benzene moiety with at least one C$_1$–C$_{20}$ alkyl group;

A is a divalent radical selected from C$_1$–C$_{10}$ alkylene, C$_2$–C$_{10}$ alkenylene, C$_2$–C$_{10}$ alkynylene, C$_1$–C$_{10}$ hydroxyalkylene, symmetric or asymmetric di-C$_1$–C$_{10}$-alkylenether, arylene, arylene-C$_1$–C$_{10}$-alkylene, or C$_1$–C$_{10}$-alkylenearyl-C$_1$–C$_{10}$ alkylene;

B is a divalent radical selected from C$_1$–C$_{10}$ alkylene, C$_2$–C$_{10}$ alkenylene, C$_2$–C$_{10}$ alkynylene, C$_1$–C$_{10}$ hydroxyalkylene, arylene, arylene-C$_1$–C$_{10}$-alkylene, or C$_1$–C$_{10}$-alkylenearyl-C$_1$–C$_{10}$-alkylene; and X$^{2-}$ is a divalent counter ion, two monovalent counter ions, or a fraction of a polyvalent counter ion sufficient to balance the cationic charge in the repeating unit which forms the ionene polymer backbone.

2. The composition of claim 1, wherein the microorganism is bacteria, fungi, or algae.

3. The composition of claim 1, wherein said salt of dodecylamine is an organic salt of dodecylamine.

4. The composition of claim 3, wherein said organic salt of dodecylamine is a carboxylic acid salt of dodecylamine.

5. The composition of claim 4, wherein said carboxylic acid is selected from the group consisting of acyclic, cyclic or aromatic mono- or dicarboxylic acids having up to ten carbon atoms.

6. The composition of claim 5, wherein said carboxylic acid salt of dodecylamine is selected from the group consisting of dodecylamine acetate, dodecylamine propionate, dodecylamine butyrate, dodecylamine citrate, dodecylamine lactate, dodecylamine valerate, dodecylamine phthalate, dodecylamine succinate, dodecylamine octanoate, dodecylamine nonanate, dodecylamine formate, dodecylamine sorbate, dodecylamine oxalate, dodecylamine laurate, dodecylamine benzoate, dodecylamine 2-hydroxybenzoate, dodecylamine 3-hydroxybenzoate, or dodecylamine 4-hydroxybenzoate.

7. The composition of claim 6, wherein said carboxylic acid salt of dodecylamine is dodecylamine acetate, dodecylamine propionate, dodecylamine butyrate, dodecylamine valerate, dodecylamine phthalate, dodecylamine succinate, dodecylamine citrate, or dodecylamine lactate.

8. The composition of claim 1, wherein said salt of dodecylamine is an inorganic salt of dodecylamine.

9. The composition of claim 8, wherein said inorganic salt of dodecylamine is dodecylamine hydrochloride.

10. The composition of claim 5, wherein said carboxylic acid salt of dodecylamine has the following general formula:

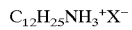

C$_{12}$H$_{25}$NH$_3^+$X$^-$ wherein X is an acyclic, cyclic, or aromatic mono- or dicarboxylic acid group having up to ten carbon atoms and which is unsubstituted or substituted.

11. The composition of claim 1, wherein the weight ratio of (a) to (b) is from about 1:99 to about 99:1.

12. The composition of claim 11, wherein the weight ratio of (a) to (b) is from about 1:30 to about 30:1.

13. The composition of claim 12, wherein the weight ratio of (a) to (b) is from about 1:2 to about 2:1.

14. The composition of claim 1, wherein said ionene polymer is poly[oxyethylene(dimethliminio)ethylene(dimethylimino)ethylenedichloride] and said salt of said dodecylamine is dodecylamine acetate.

15. The composition of claim 1, wherein R$^1$, R$^2$, R$^3$ and R$^4$ are each methyl, A is —CH$_2$CH$_2$OCH$_2$CH$_2$—, B is —CH$_2$CH$_2$—, and X$^{2-}$ is 2 Cl$^-$.

16. The composition of claim 1, wherein R$^1$, R$^2$, R$^3$ and R$^4$ are each methyl, A is —CH$_2$CH(OH)CH$_2$—, B is —CH$_2$CH$_2$— and X$^{2-}$ is 2 Cl$^-$.

17. A method of controlling the growth of at least one microorganism in or on a material or medium susceptible to attack by microorganism comprising the step of adding to the material or medium a composition comprising (a) an ionene polymer and (b) a salt of dodecylamine in a synergistically microbicidally effective combined amount to control the growth of at least one microorganism, wherein the ionene polymer comprises the repeating unit of formula I:

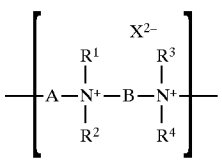

wherein

R$^1$, R$^2$, R$^3$, and R$^4$ are identical or different, and are selected from hydrogen, C$_1$–C$_{20}$ alkyl optionally substituted with at least one hydroxyl group, or benzyl optionally substituted on the benzene moiety with at least one C$_1$–C$_{20}$ alkyl group;

A is a divalent radical selected from C$_1$–C$_{10}$ alkylene, C$_2$–C$_{10}$ alkenylene, C$_2$–C$_{10}$ alkynylene, C$_1$–C$_{10}$ hydroxyalkylene, symmetric or asymmetric di-C$_1$–C$_{10}$-alkylenether, arylene, arylene-C$_1$–C$_{10}$-alkylene, or C$_1$–C$_{10}$-alkylenearyl-C$_1$–C$_{10}$ alkylene;

B is a divalent radical selected from C$_1$–C$_{10}$ alkylene, C$_2$–C$_{10}$ alkenylene, C$_2$–C$_{10}$ alkynylene, C$_1$–C$_{10}$ hydroxyalkylene, arylene, arylene-C$_1$–C$_{10}$-alkylene, or C$_1$–C$_{10}$-alkylarylene-C$_1$–C$_{10}$-alkylene; and X$^{2-}$ is a divalent counter ion, two monovalent counter ions or a fraction of a polyvalent counter ion sufficient to balance the cationic charge in the repeating unit which forms the ionene polymer backbone.

18. The method of claim 17, wherein the microorganism is selected from bacteria, fungi, and algae.

19. The method of claim 17, wherein the material or medium is wood pulp, wood chips, lumber, paint, leather, adhesive and coatings, animal hides, tanning liquor, paper mill liquor, a metalworking fluid, petrochemical, pharmaceutical formulation, cooling water, recreational water, dyes, clays, mineral slurries, cationic surfactants and formulations with cationic surfactants, influent water, waste water, pasteurizers, retort cookers, a cosmetic or toiletry formulation, textiles, a geological drilling lubricant or an agrochemical composition for crop or seed protection.

20. The method of claim 17, wherein the material or medium is in the form of a solid, dispersion, emulsion, solution or a solid.

21. The method of claim 17, wherein said salt of dodecylamine is an organic salt of dodecylamine.

22. The method of claim 21, wherein said organic salt of dodecylamine is a carboxylic acid salt of dodecylamine.

23. The method of claim 22, wherein said carboxylic acid is selected from the group consisting of acyclic, cyclic or aromatic mono- or dicarboxylic acids having up to ten carbon atoms.

24. The method of claim 23, wherein said carboxylic acid salt of dodecylamine is selected from the group consisting of dodecylamine acetate, dodecylamine propionate, dodecylamine butyrate, dodecylamine citrate, dodecylamine lactate, dodecylamine valerate, dodecylamine phthalate, dodecylamine succinate, dodecylamine octanoate, dodecylamine nonanate, dodecylamine formate, dodecylamine sorbate, dodecylamine oxalate, dodecylamine laurate, dodecylamine benzoate, dodecylamine 2-hydroxybenzoate, dodecylamine 3-hydroxybenzoate, or dodecylamine 4-hydroxybenzoate.

25. The method of claim 24, wherein said carboxylic acid salt of dodecylamine is dodecylamine acetate, dodecylamine propionate, dodecylamine butyrate, dodecylamine valerate, dodecylamine phthalate, dodecylamine succinate, dodecylamine citrate, or dodecylamine lactate.

26. The method of claim 17, wherein said salt of dodecylamine is an inorganic salt of dodecylamine.

27. The method of claim 26, wherein said inorganic salt of dodecylamine is dodecylamine hydrochloride.

28. The method of claim 23, wherein said carboxylic acid salt of dodecylamine has the following general formula:

$C_{12}H_{25}NH_3^+X^-$ wherein R is an acyclic, cyclic, or aromatic mono- or dicarboxylic acid group having up to ten carbon atoms and which is unsubstituted or substituted.

29. The method of claim 17, wherein the weight ratio of (a) to (b) is from about 1:99 to about 99:1.

30. The method of claim 29, wherein the weight ratio of (a) to (b) is from about 1:30 to about 30:1.

31. The method of claim 30, wherein the weight ratio of (a) to (b) is from about 1:2 to about 2:1.

32. The method of claim 17, wherein $R^1$, $R^2$, $R^3$ and $R^4$ are each methyl, A is —$CH_2CH_2OCH_2CH_2$—, B is —$CH_2CH_2$—, and $X^{2-}$ is 2 Cl$^-$.

33. The method of claim 17, wherein $R^1$, $R^2$, $R^3$ and $R^4$ are each methyl, A is —$CH_2CH(OH)CH_2$—, B is —$CH_2CH_2$— and $X^{2-}$ is 2 Cl$^-$.

34. A method for preventing spoilage of a material or medium caused by bacteria or fungi or algae comprising the step of adding to the material or medium a composition comprising (a) an ionene polymer and (b) a salt of dodecylamine in a synergistically microbicidally effective combined amount to prevent spoilage, wherein the ionene polymer comprises the repeating unit of formula I:

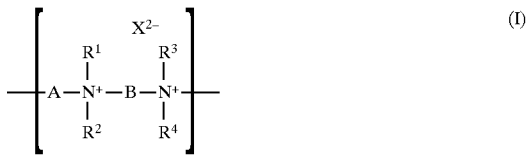

wherein $R^1$, $R^2$, $R^3$, and $R^4$ are identical or different, and are selected from hydrogen, $C_1$–$C_{20}$ alkyl optionally substituted with at least one hydroxyl group, or benzyl optionally substituted on the benzene moiety with at least one $C_1$–$C_{20}$ alkyl group;

A is a divalent radical selected from $C_1$–$C_{10}$ alkylene, $C_2$–$C_{10}$ alkenylene, $C_2$–$C_{10}$ alkynylene, $C_1$–$C_{10}$ hydroxyalkylene, symmetric or asymmetric di-$C_1$–$C_{10}$-alkylenether, arylene, arylene-$C_1$–$C_{10}$-alkylene, or $C_1$–$C_{10}$-alkylenearyl-$C_1$–$C_{10}$-alkylene;

B is a divalent radical selected from $C_1$–$C_{10}$ alkylene, $C_2$–$C_{10}$ alkenylene, $C_2$–$C_{10}$ alkynylene, $C_1$–$C_{10}$ hydroxyalkylene, arylene, arylene-$C_1$–$C_{10}$-alkylene, or $C_1$–$C_{10}$-alkylarylene-$C_1$–$C_{10}$-alkylene; and $X^{2-}$ is a divalent counter ion, two monovalent counter ions, or a fraction of a polyvalent counter ion sufficient to balance the cationic charge in the repeating unit which forms the ionene polymer backbone.

* * * * *